United States Patent
Djojo et al.

(10) Patent No.: US 7,141,670 B2
(45) Date of Patent: Nov. 28, 2006

(54) PROCESS FOR THE PREPARATION OF 1-(PYRIMIDIN-2-YL)PROPAN-2-ONES

(75) Inventors: Francis Djojo, Visp (CH); Gareth J. Griffiths, Visp (CH); Yves Guggisberg, Miège (CH); Hidetaka Hiyoshi, Nakanogo (JP)

(73) Assignees: Lonza Ltd., Basel (CH); Ihara Chemical Industry Co., Ltd., Shizuoka (JP)

( * ) Notice: Subject to any disclaimer, the term of this patent is extended or adjusted under 35 U.S.C. 154(b) by 483 days.

(21) Appl. No.: 10/491,281

(22) PCT Filed: Oct. 9, 2002

(86) PCT No.: PCT/EP02/11280

§ 371 (c)(1),
(2), (4) Date: Mar. 31, 2004

(87) PCT Pub. No.: WO03/033475

PCT Pub. Date: Apr. 24, 2003

(65) Prior Publication Data

US 2004/0242877 A1   Dec. 2, 2004

(30) Foreign Application Priority Data

Oct. 15, 2001   (EP) .................... 01124587

(51) Int. Cl.
*C07D 239/52*   (2006.01)
*C07D 305/10*   (2006.01)

(52) U.S. Cl. ..................................... 544/319
(58) Field of Classification Search .............. 544/319
See application file for complete search history.

(56) References Cited

U.S. PATENT DOCUMENTS 4,874,873 A   10/1989   Woolard

FOREIGN PATENT DOCUMENTS

| DE | 24 26 913 A1 | 12/1975 |
|---|---|---|
| DE | 2426913 | 12/1975 |
| DE | 27 05 562 | 8/1978 |
| DE | 2705562 | 8/1978 |
| EP | 0 024 200 | 2/1981 |
| EP | 0024200 | 2/1981 |
| GB | 1593822 | 7/1981 |

*Primary Examiner*—Deepak Rao
(74) *Attorney, Agent, or Firm*—Fisher Christen & Sabol

(57) ABSTRACT

A process for the preparation of 1-(pyrimidin-2-yl)propan-2-ones of general formula (I), in which R is in each case a $C_{1-10}$-alkyl group, a $C_{3-8}$-cycloalkyl group, an alkyl group or an aryl-$C_{1-4}$-alkyl group. For this, a malondiimidate of the general formula (II), in which R has the meaning given above, is reacted with diketene. The compounds which can be prepared according to the invention are intermediates for the synthesis of agrochemical active ingredients.

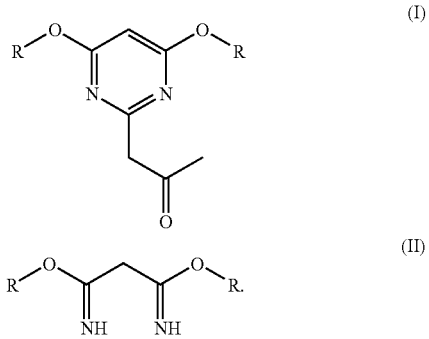

10 Claims, No Drawings

PROCESS FOR THE PREPARATION OF 1-(PYRIMIDIN-2-YL)PROPAN-2-ONES

This is a 371 national stage application of International Patent Application No. PCT/EP02/11280, filed on Oct. 9, 2002, that has priority benefit of European Patent Application No. 01124587.5, filed on Oct. 15, 2001.

The invention relates to a process for the preparation of 1-(pyrimidin-2-yl)propan-2-ones of the general formula

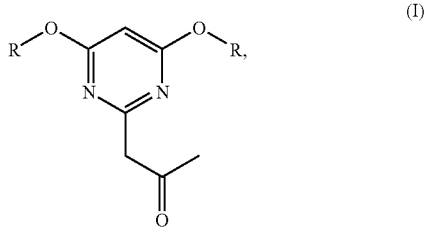

(I)

in which R is in each case a $C_{1-10}$-alkyl group, a $C_{3-8}$-cycloalkyl group, an ally group or an aryl-$C_{1-4}$-alkyl group. $C_{1-10}$-Alkyl groups are understood here and below as meaning all linear or branched primary, secondary or tertiary alkyl groups having 1 to 10 carbon atoms, thus, for example, methyl, ethyl propyl, isopropyl, butyl, isobutyl sec-butyl, tert-butyl, pentyl isopentyl, tert-pentyl, neopentyl hexyl, heptyl, octyl, nonyl or decyl.

$C_{3-8}$-Cycloalkyl are to be understood as meaning, in particular, cyclopropyl, cyclobutyl, cyclopentyl, cyclohexyl, cycloheptyl and cyclooctyl.

Aryl-$C_{1-4}$-alkyl groups are the groups composed of an aryl group and an alkyl group having 1 to 4 carbon atoms, aryl groups being understood as meaning, in particular, phenyl or naphthyl groups. The aryl groups may also be substituted by one or more $C_{1-4}$-alkyl groups, $C_{1-4}$-alkoxy groups or halogen atoms. Examples of aryl-$C_{1-4}$-alkyl groups are, in particular, benzyl, 1-phenylethyl, 2-phenylethyl and 3-phenylpropyl.

Compounds of the formula I, in particular the dimethoxy compound (R=Me) are potential intermediates in the synthesis of agrochemical active ingredients.

Syntheses of these compounds have hitherto not been described in the prior art.

It was an object of the present invention to provide a preparation process which is simple and suitable for an industrial scale.

According to the invention, the object is achieved by the process of the invention. It has been found that the malondiimidates, which are readily available from malodinitrile and the corresponding alcohols (DE-A-24 26 913, EP-A-0 024 200), of the general formula:

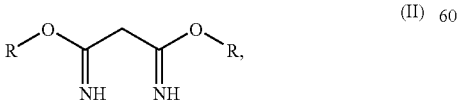

(II)

in which R has the meaning given above, react with diketene of the formula:

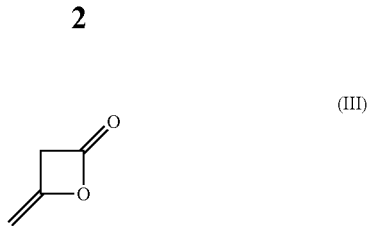

(III)

directly and in a good yield to give the desired compounds (I).

The malondiimidates (II) can either be used without a diluent (as free base) or else be formed in situ from a corresponding salt and a base. The latter may be an inorganic base or an organic base such as a tertiary amine. The malondiimidates are preferably used without a diluent. For this, they can, for example, be extracted with a solvent of low polarity, such as dichloromethane or diethyl ether, from a neutralized solution of one of their salts and be isolated by evaporating the solvent (EP-A0 024 200).

The salts of the malondiimidates (II) used are preferably the dihydrochlorides.

The process according to the invention is preferably used for the preparation of 1-(4,6-dimethoxypyrimidin-2-yl)propan-2-one, by using dimethyl malondiimidate (R=Me) as malondiimidate (II).

The process according to the invention is advantageously carried out in a solvent which is essentially inert under the reaction conditions, such as, for example, aromatic hydrocarbons like toluene or xylene or ketones like acetone. The reaction temperature is advantageously 50 to 150° C. for the aromatic solvents or 0 to 100° C. for ketone solvents.

The examples below illustrate how the process according to the invention is carried out, but are not intended to impose any limitation.

EXAMPLE 1

1-(4,6-Dimethoxypyrimidin-2-yl)propan-2-one

A solution of dimethyl malondiimidate (80 g, 0.61 mol) in toluene (240 ml) was heated to 80° C. Diketene (103.44 g, 1.23 mmol) was added over the course of 2 h, the temperature being held at 80° C. The reaction mixture was held at 80° C. for a further 2 h and then cooled to room temperature. Following the addition of water (200 ml), it was stirred for 0.5 h and then the phases were separated. The aqueous phase was extracted with toluene (590 ml) and the combined organic phases were dried over sodium sulfate. Filtration and evaporation of the solvent in vacuo gave 117.3 g of crude product in the form of a reddish liquid. The crude product was purified by distillation on a 20 cm Vigreux column.

Yield: 61.29 g, purity (GC)>98% (55% of theory, based on dimethyl malondiimidate). B.p.: 90° C./0.4 mbar $^1$H NMR (CDCl$_3$): δ=5.92 (s, 1H); 3.91 (s, 6H); 3.86 (s, 2H); 2.27 (s, 3H). In addition, the spectrum also has the signals of the enol form.

EXAMPLE 2

1-(4,6-Dimethoxypyrimidin-2-yl)propan-2one

Dimethyl malondiimidate dihydrochloride (90.0 kg, 443 mol, 1 eq) and acetone (330 l) were placed under nitrogen in a 630 l stirred vessel. The suspension was cooled to 0 to 5° C. and triethylamine (98.7 k, 975 mol, 2.2 eq) was added over the course of 120 min at 0 to 5° C. The suspension was stirred for another 30 min at 0 to 5° C. and then warmed to 25° C. Diketene (44.7 kg, 531 mol. 1.2 eq) was added within 90 min at ca. 25° C. After the addition the mixture was heated to 30° C. and after 2 h reaction time at the same temperature the excess diketene was destroyed by adding methanol (15 l) and 4-(dimethylamino)pyridine (0.5 kg). The precipitated trimethylammonium chloride (ca. 160 kg) was filtered off and the filter cake was washed with acetone (2×113 l). The combined filtrates were concentrated by distilling off acetone (450–500 l) at ambient pressure. The residual solution was cooled to 40° C. and water (198 l) was added. In order to remove the acetone completely, the solution was subjected to another distillation at 100 to 200 mbar until a head temperature of ca. 45° C. had been reached (after ca. 5 h) and ca 150–180 l of distillate had been obtained. The residue was cooled to 30° C., seeded by adding 1-(4,6-dimethoxypyrimidin-2-yl)propan-2-one crystals (0.6 kg) and subsequently cooled to 0° C. within 60 min. After another 60 min at 0° C. the product was filtered, washed with cold water (135 l) and dried at 35° C./<100 mbar (16 h).

Yield: 49 kg (55%) slightly yellowish solid, purity >95%.

The invention claimed is:

1. A process for the preparation of a 1-(pyrimidin-2-yl) propan-2-one of the formula:

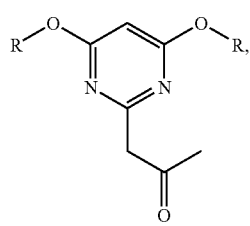

in which R is in each case a $C_{1-10}$-alkyl group, a $C_{3-8}$-cycloalkyl group, an allyl group or an aryl-$C_{1-4}$-alkyl group, comprising reacting a malondiimidate of the formula:

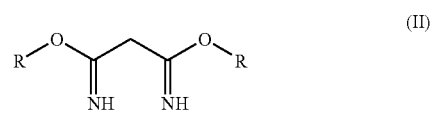

in which R has the meaning given above, with diketene of the formula:

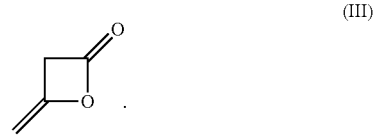

2. The process according to claim 1, wherein the malondiimidate (II) is prepared in situ from a corresponding salt and a base.

3. The process according to claim 2, wherein the salt of the malondiimidate (II) used is the dihydrochloride.

4. The process according to claim 3, wherein the base is a tertiary amine.

5. The process according to claim 4, wherein the malondiimidate (II) used is dimethyl malondiimidate.

6. The process according to claim 2, wherein the base is a tertiary amine.

7. The process according to claim 4, wherein the malondiimidate (ii) used is dimethyl malondiimidate.

8. The process according to claim 5 wherein, in the compounds of formulae (I) and (II), R in each case is methyl.

9. The process according to claim 1, wherein the reaction is carried out in a solvent that is essentially inert under reaction conditions.

10. The process according to claim 9, wherein the solvent is an aromatic hydrocarbon or a ketone.

* * * * *